US008629415B2

(12) United States Patent
Fadler (10) Patent No.: US 8,629,415 B2
(45) Date of Patent: Jan. 14, 2014

(54) RADIATION THERAPY APPARATUS

(75) Inventor: Franz Fadler, Hetzles (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/434,634

(22) Filed: Mar. 29, 2012

(65) Prior Publication Data

US 2013/0090514 A1 Apr. 11, 2013

(30) Foreign Application Priority Data

Mar. 30, 2011 (DE) .......................... 10 2011 006 451

(51) Int. Cl.
*G21K 5/04* (2006.01)
(52) U.S. Cl.
USPC .................. 250/492.1; 250/491.1; 250/492.3; 600/1; 600/2; 600/3
(58) Field of Classification Search
USPC .......................... 250/492.1, 492.3; 600/1, 2, 3
See application file for complete search history.

(56) References Cited

U.S. PATENT DOCUMENTS

| 5,751,781 | A | 5/1998 | Brown et al. |
| 6,865,254 | B2 | 3/2005 | Näfstadius |
| 6,969,194 | B1 | 11/2005 | Näfstadius |
| 7,295,648 | B2 | 11/2007 | Brown |
| 7,318,805 | B2 | 1/2008 | Schweikard et al. |
| 7,466,792 | B2 | 12/2008 | Bakai et al. |
| 7,679,073 | B2 | 3/2010 | Urano et al. |
| 2008/0315111 | A1* | 12/2008 | Sommer ................... 250/396 R |
| 2012/0035470 | A1* | 2/2012 | Kuduvalli et al. ............ 600/427 |

FOREIGN PATENT DOCUMENTS

| DE | 203 04 631 U1 | 7/2003 |
| DE | 10 2005 018 330 A1 | 10/2006 |

OTHER PUBLICATIONS

German Office Action dated Jan. 4, 2012 for corresponding German Patent Application No. DE 10 2011 006 451.6 with English translation.

* cited by examiner

*Primary Examiner* — Nicole Ippolito
(74) *Attorney, Agent, or Firm* — Lempia Summerfield Katz LLC

(57) ABSTRACT

A radiation therapy apparatus includes a gantry having a central aperture that defines a cavity, in which a patient is positionable. The apparatus also includes a positioning device, with which the patient is positionable in the central aperture of the gantry, and a radiation head for generating therapeutic radiation. The apparatus includes an extension mechanism for the radiation head. The extension mechanism may be operated, such that in a first operating mode, the radiation head is disposable inside the gantry, such that the gantry has, on a side facing the positioning device, a front surface that constitutes a front limit of the radiation therapy apparatus toward the positioning device. In the first operating mode, the radiation head is behind the front surface viewed from the positioning device. In a second operating mode, the radiation head, viewed from the positioning device, may be moved out in front of the front surface.

20 Claims, 9 Drawing Sheets

RADIATION THERAPY APPARATUS

This application claims the benefit of DE 10 2011 006 451.6, filed on Mar. 30, 2011.

BACKGROUND

The present embodiments relate to a radiation therapy apparatus for treating tumor diseases.

In a radiation therapy apparatus, a gantry may be used to position a radiation head, from which therapeutic radiation is directed at a patient, around the patient.

Different gantry designs are known.

U.S. Pat. No. 5,751,781 discloses an annular gantry with a central cylindrical aperture, in which a patient may be positioned for irradiation. Inside the gantry, the radiation head may be rotated along a plane of rotation, thereby enabling radiation to be directed at the patient from different directions.

U.S. Pat. No. 6,969,194 and U.S. Pat. No. 6,865,254 disclose gantry designs having a front and a rear supporting gantry (e.g., two supporting gantries). The radiation head may be positioned at different positions between the two supporting gantries. A patient may be positioned between the two supporting gantries for irradiation.

SUMMARY AND DESCRIPTION

The present embodiments may obviate one or more of the drawbacks or limitations in the related art. For example, a radiation therapy apparatus that has a simple gantry design, while allowing flexible adjustment of the position of a radiation head, is provided.

The radiation therapy apparatus according to the present embodiments includes a gantry having a central aperture that defines a space, in which a patient may be positioned for irradiation. The radiation therapy apparatus also includes a positioning device, with which the patient may be positioned in the central aperture of the gantry, and a radiation head for generating therapeutic radiation that is directed at the patient. The radiation therapy apparatus includes an extension mechanism for the radiation head. The extension mechanism moves the radiation head and may be operated such that different operating modes may be set.

In a first operating mode of the radiation therapy apparatus, the radiation head is disposed inside the gantry, the gantry having a front surface on a side facing the positioning device. In the first operating mode, the front surface constitutes a front edge of the radiation therapy apparatus toward the positioning device. For example, in the first operating mode, there are no energy generating components (e.g., the radiation head) projecting from the front surface that may collide, for example, with the patient or with the positioning device.

The radiation head and/or other space occupying, energy generating components are disposed behind the front surface (viewed from the positioning device). In the best-case scenario, no components project beyond the front surface in the first operating mode. The front surface therefore constitutes the limit of the radiation therapy apparatus in relation to the positioning device. Provided the patient and the positioning device are located in front of the front surface, collisions with rotating components of the gantry are not possible in the first operating mode.

In a second operating mode, the radiation head is moved out using the extension mechanism (e.g., in front of the front surface (viewed from the positioning device), which in the first operating mode constitutes the limit of the radiation therapy apparatus toward the positioning device). In the second operating mode, there is therefore a risk of components that project from the front surface colliding with the positioning device or with a patient positioned thereon. However, the outward movement of the radiation head increases the spatial possibilities for applying the radiation, making irradiation altogether more flexible. The number of possible irradiation angles and irradiation directions may be increased.

The gantry may be, for example, annular in shape (e.g., similar to a conventional computed tomography gantry) having a central aperture. The cavity defined by the central aperture is approximately cylindrical. Inside the gantry disposed around the cavity, the radiation head may be rotated about a central axis, thereby enabling the radiation head to be moved to different positions within the plane of rotation. The axis of rotation may coincide with the longitudinal axis of the cylindrical aperture.

Using the extension mechanism, the radiation head, which may otherwise only be rotated in the plane of rotation inside the gantry, may be moved out of the plane of rotation, thereby executing a movement having a component that is perpendicular to the plane of rotation (e.g., points in the direction of the axis of rotation).

In contrast to U.S. Pat. No. 6,865,254, similar movements of the radiation head are possible without necessitating a complex and space-occupying design with two supporting gantries.

Using the extension mechanism, the radiation head is therefore cantilevered out of the gantry from a retracted position and may then project at least partially from the front surface of the gantry. The extension mechanism may therefore bring about a radiation head movement having a component in the direction of the longitudinal axis of the cavity, without the gantry surrounding the cavity having to be rotated. The gantry structure as such (e.g., the gantry ring carrying the radiation head) may remain spatially fixed, and the extension mechanism may be operated in order to place the radiation head in a projecting position by a movement relative to the gantry.

In one embodiment, on the side facing away from the positioning device, the gantry may have a back surface that in the first operating mode, constitutes a rear limit of the gantry. The extension mechanism may be operated such that, in a third operating mode of the radiation therapy apparatus, the radiation head may be moved out behind the back surface (viewed from the positioning device), which in the first operating mode constitutes the rear limit, by the extension mechanism.

In the first operating mode, the back surface therefore constitutes, similarly to the front surface, a limit in the sense that the radiation head and/or other space occupying, radiation generating components are disposed in front of the back surface (viewed from the positioning device). In the best case scenario, in the first operating mode, no components project beyond the back surface. The back surface and the front surface therefore represent gantry boundaries, within which, in the first operating mode, the essential components for radiation generation and/or imaging are disposed. It is in the second or third operating mode that a gantry configuration with projecting components (e.g., with a projecting radiation head) is produced by the extension mechanism.

In one embodiment, the gantry may be tilted about a horizontal axis. The gantry may be mounted on a stand, for example, via a swivel joint enabling the gantry to be tilted horizontally. The movement of the radiation head executable by the extension mechanism may be superimposed on the tilting movement of the gantry about the horizontal axis.

The central aperture of the gantry may have a longitudinal axis. The longitudinal axis may specify, for example, the direction, along which the positioning device is to be moved in order to position a patient in the aperture. In the case of a cylindrical aperture, the longitudinal axis may be the cylinder's longitudinal axis. The extension mechanism may be embodied such that the extension mechanism allows a translatory movement of the radiation head along a direction having a component along the longitudinal axis.

In one embodiment, the extension mechanism is embodied such that only a translatory movement of the radiation head in the direction of the longitudinal axis is provided. This arrangement may be embodied mechanically (e.g., via a rail system).

In a mechanically more complex embodiment, the extension mechanism is configured such that, in addition to the translatory movement, another movement of the radiation head may be executed. The other movement has a component in a direction perpendicular to the translatory movement. In this way, the distance of the radiation head from the patient or from the central axis of the radiation therapy apparatus may be increased or reduced.

The extension mechanism may also be embodied such that, in addition to the translatory movement, a tilting movement of the radiation head may be executed. With this embodiment, the radiation head may be tilted relative to the extension mechanism. This enables the direction, in which the therapeutic treatment beam is emitted, to be adjusted.

The extension mechanism may be configured such that, when the extension mechanism is extended out, the radiation head is moved along an isocentric circular segment. The focal point of the therapeutic radiation (e.g., the origin of the therapeutic radiation) thus maintains the same distance from the isocenter. By appropriate tilting of the radiation head, the central beam of the therapeutic radiation remains aligned isocentrically (e.g., toward the isocenter) even in the extended state.

DETAILED DESCRIPTION OF THE DRAWINGS

Figure 1:
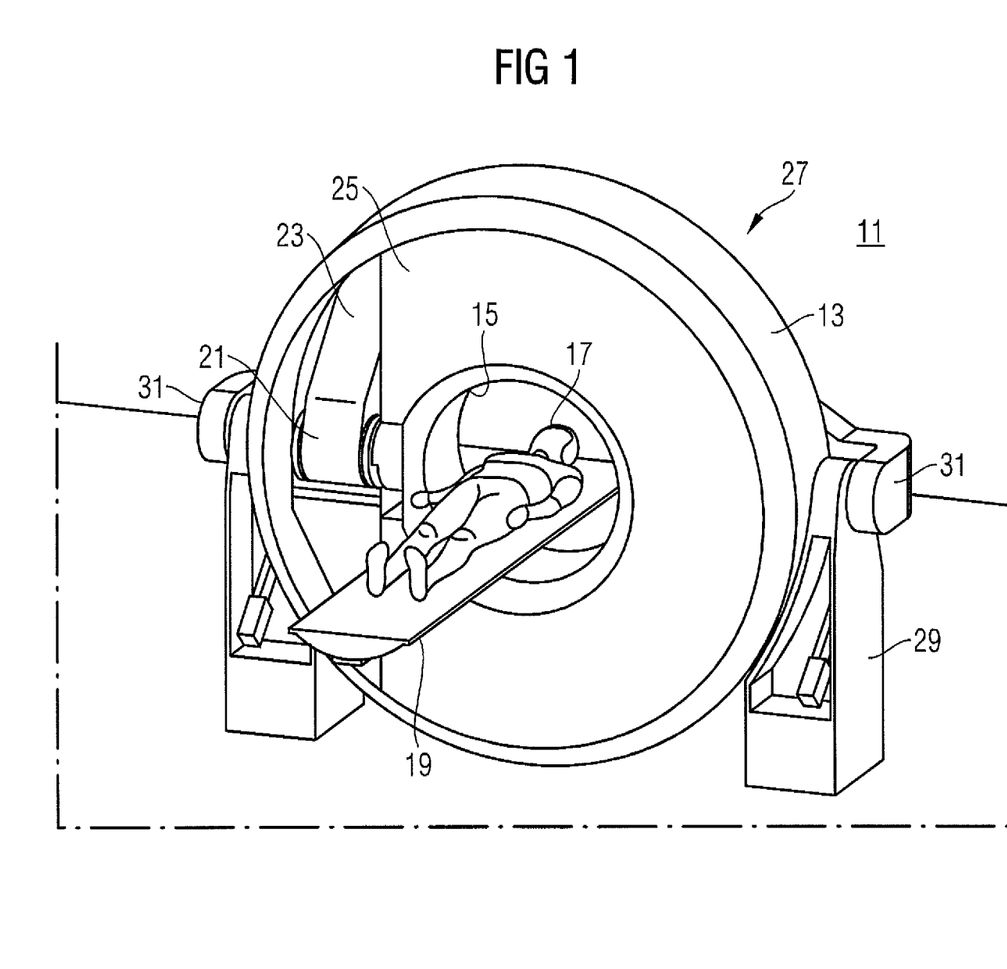
FIG. 1 shows an embodiment of a radiation therapy apparatus with a radiation head in a retracted position.

FIG. 1 shows an embodiment of a radiation therapy apparatus 11 with a radiation head in a retracted position.

The radiation therapy apparatus 11 shown in FIG. 1 has an annular gantry 13 enclosing a central aperture 15 (e.g., a cylindrical aperture). In the central aperture 15, a patient 17 may be positioned from one side using a positioning device 19 located on one side of the radiation therapy apparatus 11.

Disposed within the gantry ring 13 are components of the radiation therapy apparatus 11 (e.g., a radiation source for therapeutic irradiation, a collimator for beam limiting, an imaging device for diagnostic X-radiation and/or a detector for portal imaging). For the sake of clarity, only a radiation head 21 and an extension mechanism 23 for the radiation head 21 are shown. These components may be rotated inside a circular ring of the gantry 13. An axis of rotation coincides with a longitudinal axis of the cylindrical aperture 15. A plane of rotation runs parallel to a plane of the gantry ring 13, thereby enabling an irradiation direction of the therapeutic radiation to be adjusted.

The gantry ring 13 has, parallel to the plane of rotation, an annular front surface 25 that is a limit of the gantry ring 13 on a positioning device 19 side. In a first operating mode, which is shown in FIG. 1, no components (e.g., no radiation generating components such as the radiation head 21) project beyond a front surface 25.

As all the components are located inside the gantry ring 15, these components may also be rotated without risk of collision with a patient 17 or with the positioning device 19.

In the first operating mode, coplanar irradiation may take place, as the radiation is emitted from a point located in a plane that contains the isocenter, and is perpendicular to the longitudinal axis of the cylindrical aperture 15.

The gantry ring 13 has, also parallel to the plane of rotation, a back surface 27 that constitutes a limit of the gantry ring 13 on a side facing away from the positioning device 19. In the first operating mode, no components (e.g., no radiation generating components) project beyond the back surface 27.

In the first operating mode, the radiation therapy apparatus 11 has a configuration similar to a computed tomography scanner (CT configuration).

The annular gantry 15 is mounted on a stand 29. The annular gantry 15 may be tilted as a whole about a horizontal axis via a right- and a left-hand bearing 31, thereby tilting the plane of rotation of the gantry 15.

Figure 2:
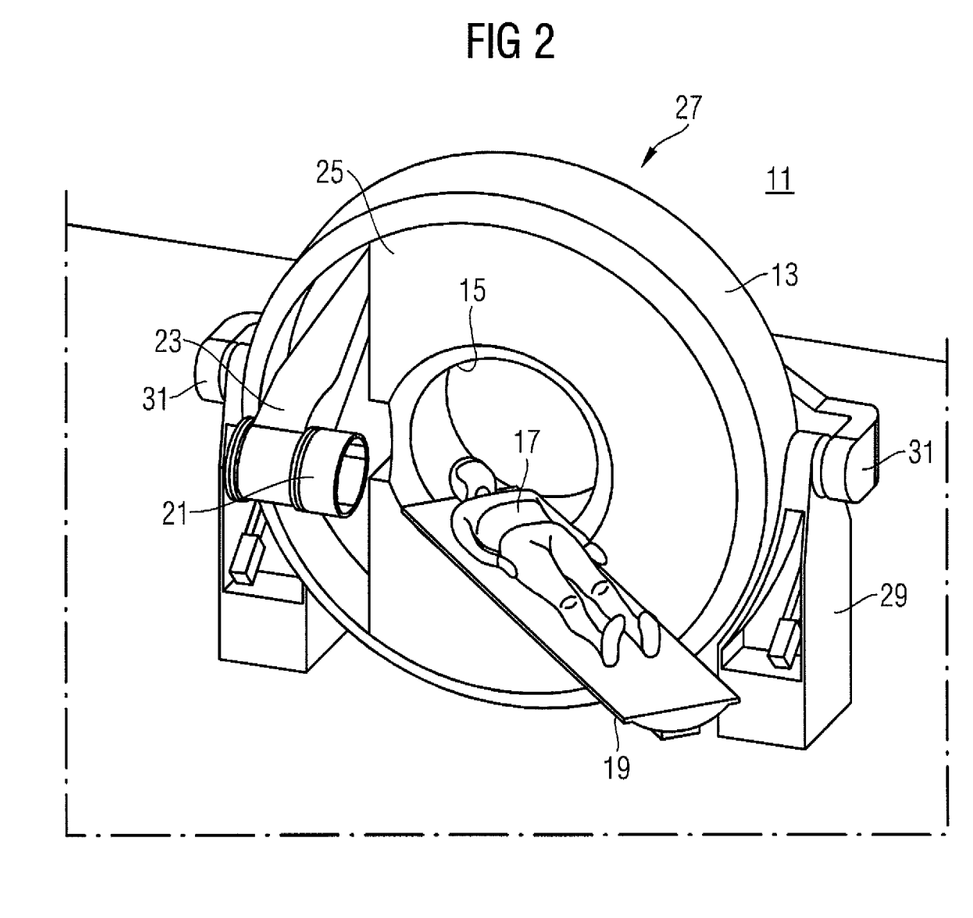
FIG. 2 shows one embodiment of the radiation therapy apparatus from FIG. 1 with the radiation head in an extended position.

FIG. 2 shows the radiation therapy apparatus 11 depicted in FIG. 1 in a second operating mode. The radiation head 21 is moved out from the gantry ring 13 by an extension mechanism 23. The radiation head 21 is viewed from the positioning device 19, in front of the front surface 25 of the gantry 13. The radiation head 21 extends beyond the front surface 25, being "cantilevered out." The configuration of the radiation therapy apparatus 11 is similar to an L-shaped configuration of conventional radiation therapy equipment with a cantilevering arm.

In this position, the irradiation may be non-coplanar, as the radiation head 21 is no longer in the plane of rotation that is characterized by the rotation of the radiation head 21 inside the gantry 13 in the first operating mode and in which the isocenter lies.

The extension mechanism 23 enables the radiation head 21 to be moved out of the plane that is perpendicular to the longitudinal axis of the gantry aperture 15 and contains the isocenter, without the gantry 13 as a whole being moved or tilted. The gantry ring 13 remains in the same position. The extension mechanism 23 causes the radiation head 21 to be moved relative to the gantry 13.

Figure 3:
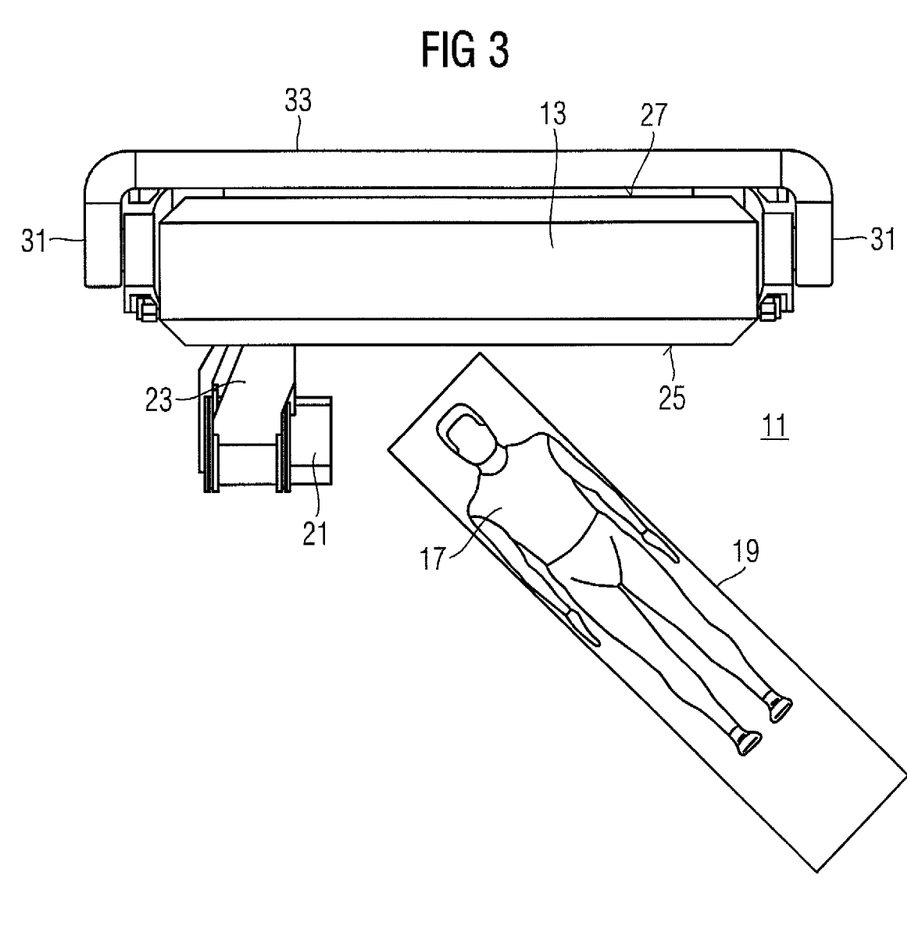
FIG. 3 shows a top view of one embodiment of the radiation therapy apparatus from FIG. 2.

FIG. 3 shows a top view of the configuration of the radiation therapy apparatus 11 shown in FIG. 2. FIG. 3 shows the cantilevered radiation head 21, which has been moved out of the plane of rotation and projects in front of the front surface 25 of the gantry 13. In FIG. 3, the back surface 27 of the gantry 13 is shown more clearly (e.g., the rear boundary of the gantry ring 13).

Also shown in FIG. 3 is a retaining structure 33 provided for mechanical reasons behind the back surface 27 of the gantry 13, although this structure is not necessary. The retaining structure 33 contains no beam shaping or radiation generating components.

Figure 4:
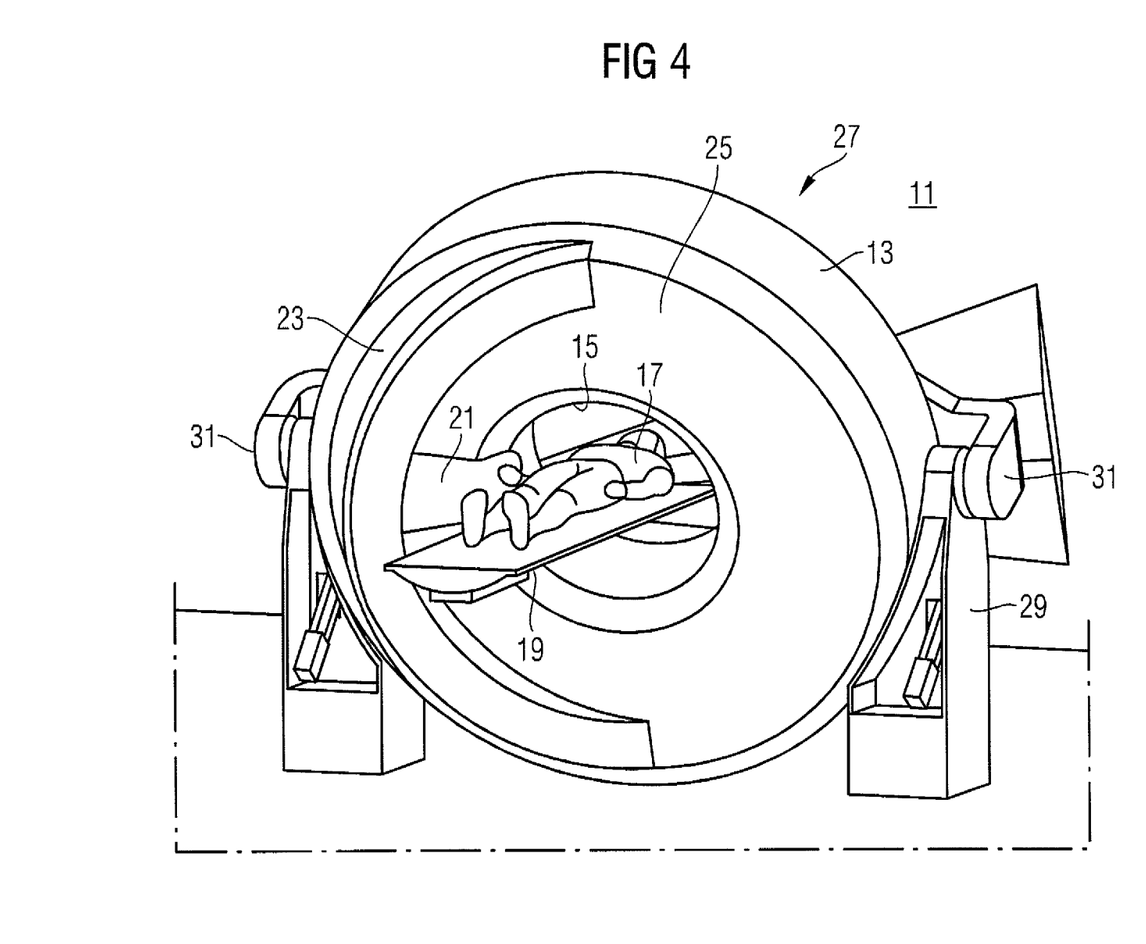
FIG. 4 shows another embodiment of the radiation therapy apparatus with an isocentrically extendable radiation head.

FIG. 4 shows another embodiment of the radiation therapy apparatus 11. The extension mechanism 23 is embodied as a semicircular segment disposed concentrically to the gantry ring 13. The radiation head 21 is disposed on the semicircular segment. The semicircular segment incorporating the radiation head 21 may be swung out from the gantry ring 13 so that the radiation head 21 is brought in front of the front surface 25 of the radiation therapy apparatus 11 by this movement. Non-coplanar isocentric irradiation may be carried out.

The difference compared to the apparatus shown in FIG. 1 is in the extension mechanism 23. Whereas the extension mechanism shown in FIG. 1 allows purely linear displacement of the radiation head 21 in a direction orthogonal to the plane of rotation, the extension mechanism shown in FIG. 4 permits isocentric motion.

The radiation head 21 may always be at the same distance from the isocenter, and the central ray of the therapeutic radiation may always be aligned to the isocenter. The central ray is tilted out from the gantry ring 13. This may be effected via a real pivoted joint.

The extension mechanism 23 may be embodied so as to execute the same or a similar movement as in the case of implementation with a real pivoted joint, using a virtual pivoted joint.

Figure 5:
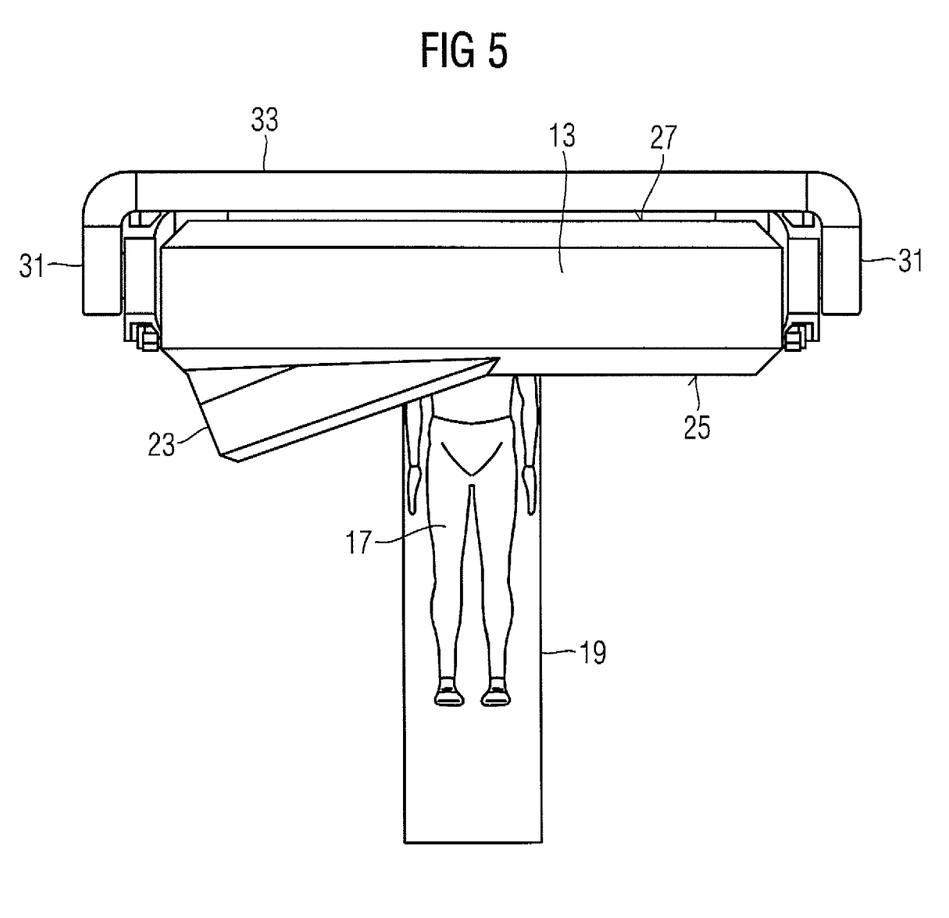
FIG. 5 shows a top view of one embodiment of the radiation therapy apparatus from FIG. 4.

FIG. 5 shows a top view of the embodiment of the radiation therapy apparatus 11 shown in FIG. 4. The cantilevering, semicircular segment 23 that carries the radiation head 21 is shown in FIG. 4. The cantilevering, semicircular segment 23 is moved out of the plane of rotation and projects in front of the front surface 25 of the gantry 13, which in the first operating mode, constitutes the limit of the gantry 13 toward the patient 17.

Figure 6A:
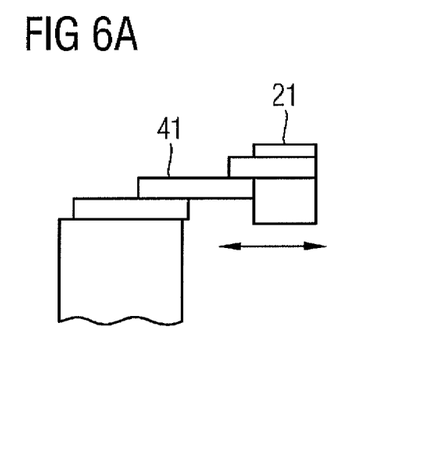
FIGS. 6a and 6b, FIGS. 7a and 7b, and FIGS. 8a and 8b show a side view and a perspective view, respectively, of different exemplary extension mechanisms based on a linear principle.
Figure 6B:
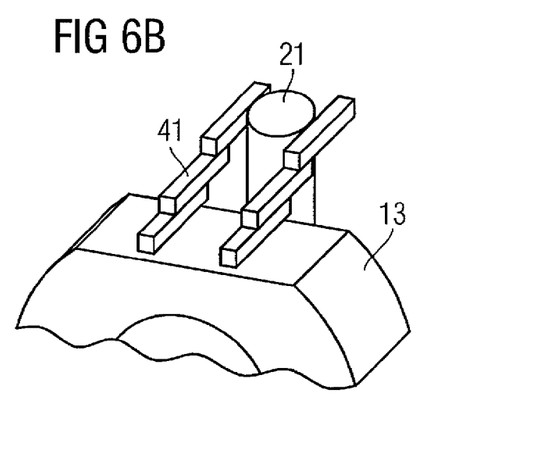

FIGS. 6a and 6b show a side view and a perspective view, respectively, of an extension mechanism that moves the radiation head 21 linearly using a rail system 41.

Figure 7A:
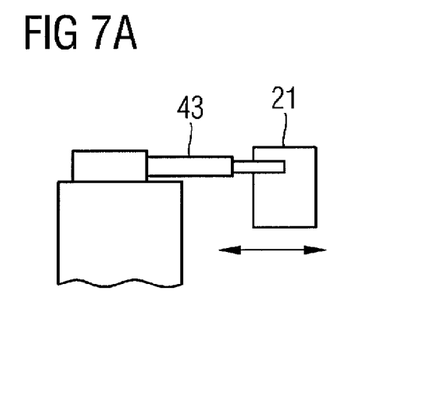
Figure 7B:
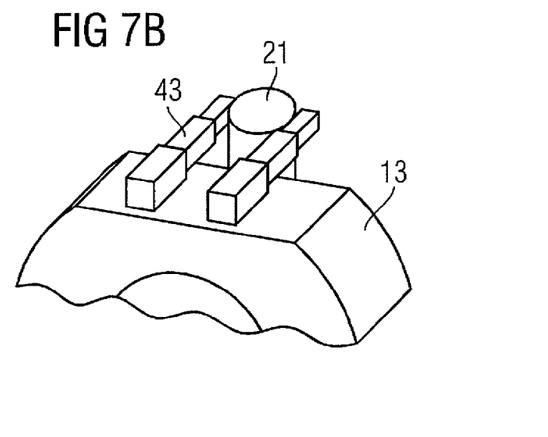

FIGS. 7a and 7b show a side view and a perspective view, respectively, of an extension mechanism that moves the radiation head 21 linearly using telescopic cylinders 43.

Figure 8A:
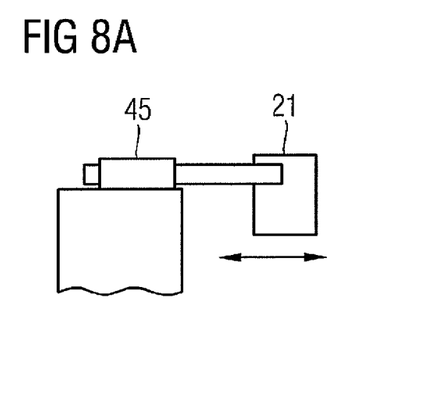
Figure 8B:
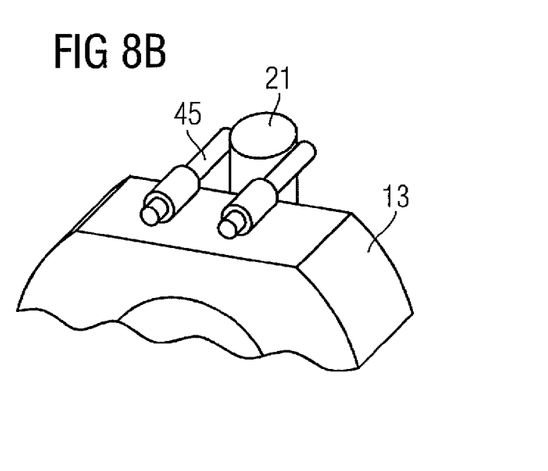

FIGS. 8a and 8b show a side view and a perspective view, respectively, of an extension mechanism that moves the radiation head 21 linearly using ball screws 45, the travel being comparatively short.

The drives shown in FIGS. 6 to 8 are based on serial kinematics. The main motion of the individual components is a linear movement.

Figure 9:
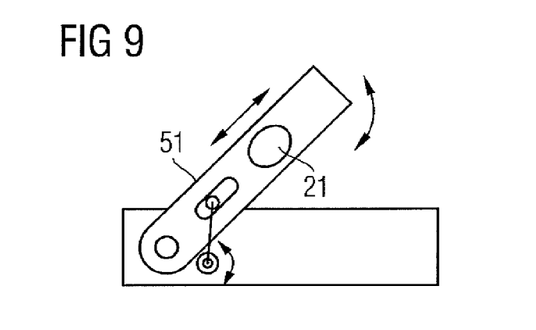
FIG. 9, FIGS. 10a and 10b, FIGS. 11a and 11b, FIGS. 12a and 12b, and FIG. 13 show top views or perspective views of different exemplary extension mechanisms based on a rotatory principle.

FIG. 9 shows a top view of an extension mechanism that moves the radiation head 21 out using a swiveling cantilever arm 51. The radiation head 21 may be moved linearly relative to the cantilever arm 51.

Figure 10A:
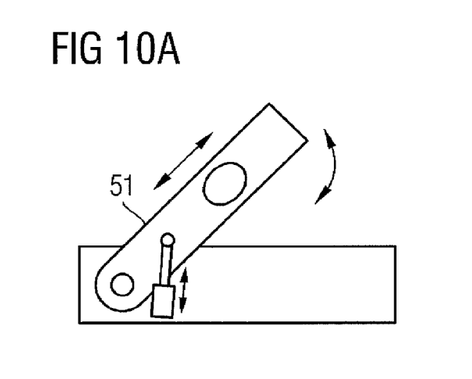
Figure 10B:
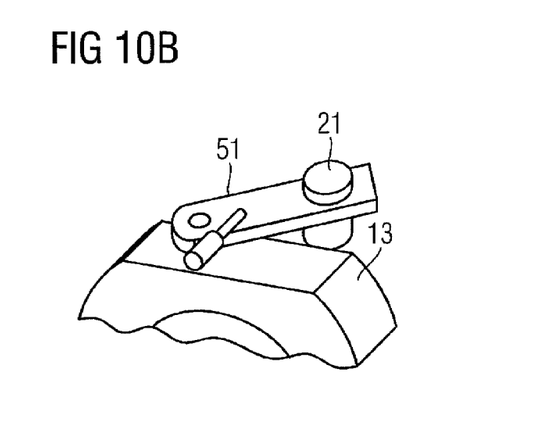

FIGS. 10a and 10b show a top view and a perspective view, respectively, of an extension mechanism that moves the radiation head 21 out using a cantilever arm 51 that is operable to swivel.

Figure 11A:
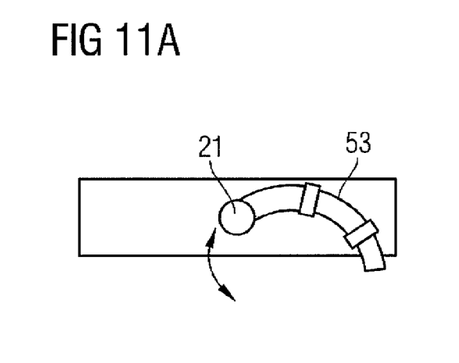
Figure 11B:
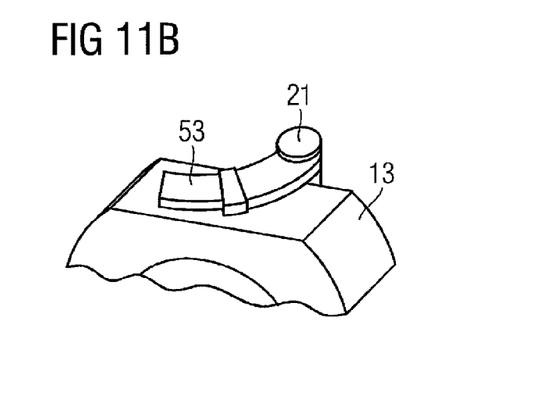

FIG. 11a and FIG. 11b show a top view and a perspective view, respectively, of an extension mechanism that moves the radiation head 21 out using a circular rail 53.

Figure 12A:
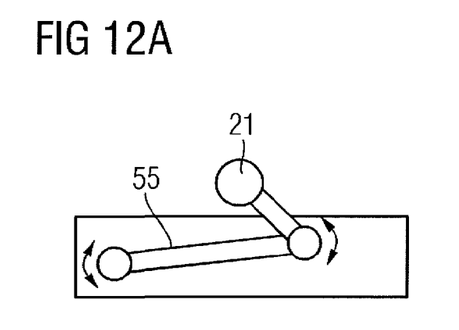
Figure 12B:
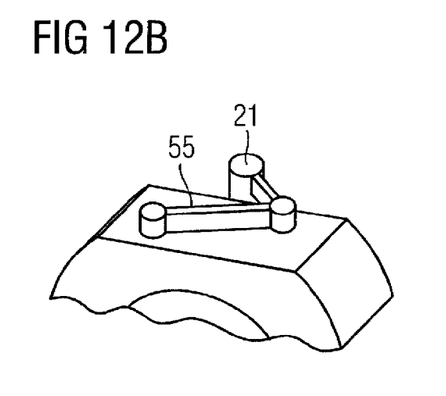

FIG. 12a and FIG. 12b show a top view and a perspective view, respectively, of an extension mechanism that moves the radiation head 21 out using pivot mounted arms 55 operating on the selective compliant articulated robot arm or selective compliant assembly robot arm (SCARA) principle.

Figure 13A:
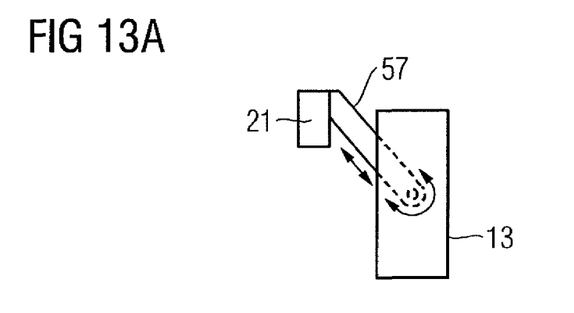
Figure 13B:
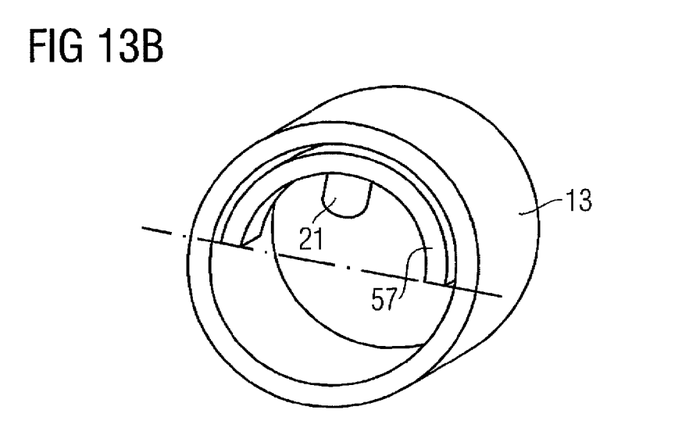

FIG. 13a and FIG. 13b show a side view and a perspective view, respectively, of an extension mechanism with a swing-out semicircular element 57.

The drives shown in FIGS. 9 to 13 are based on serial kinematics. The main motion of the individual components is a rotatory movement.

Figure 14:
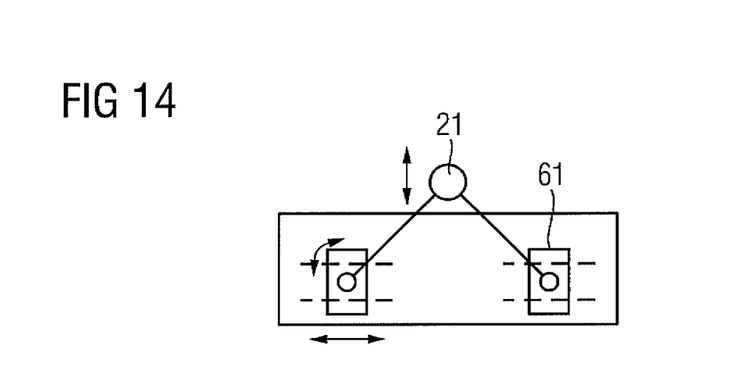
FIG. 14 and FIG. 15 each show a plan view of different exemplary extension mechanisms based on a linear principle with movement in opposite directions.

FIG. 14 shows a plan view of an extension mechanism that employs rail-mounted slides 61 that may be moved in opposite directions to one another.

Figure 15:
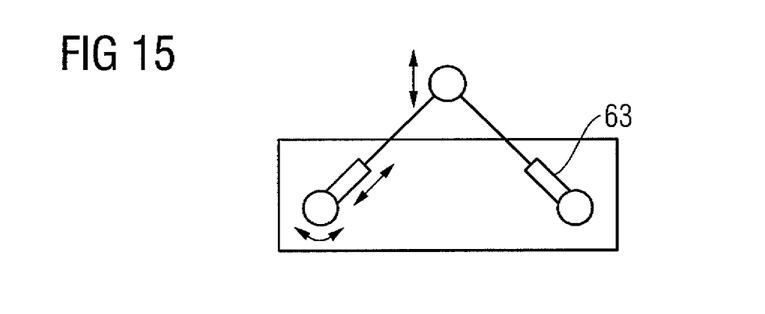

FIG. 15 shows a plan view of an extension mechanism that employs cylinder plungers 63 that may be moved parallel to one another.

Figure 16:
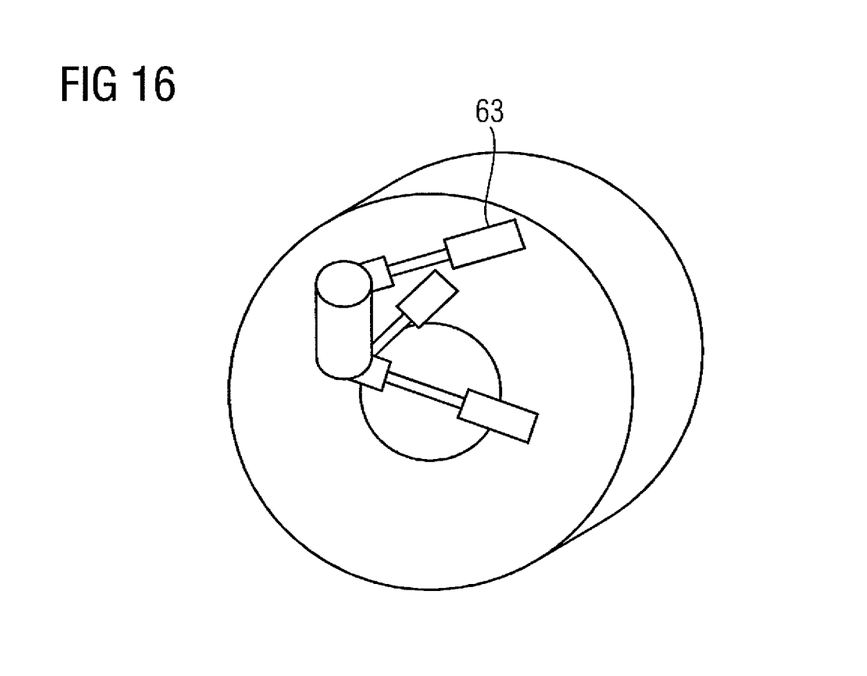
FIG. 16 shows a perspective view of one embodiment of an extension mechanism with three cylinders disposed in a tripod-like manner.

FIG. 16 shows a perspective view of an extension mechanism with three cylinder plungers 63 disposed in a tripod-like manner.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A radiation therapy apparatus comprising:
    a gantry comprising a central aperture that defines a cavity, in which a patient is positionable for irradiation;
    a positioning device, with which the patient is positionable in the central aperture of the gantry;
    a radiation head for generating therapeutic radiation that is directable at the patient; and
    an extension mechanism for the radiation head,
    wherein the extension mechanism is configured such that, in a first operating mode of the radiation therapy apparatus, the radiation head is disposed inside the gantry such that the gantry has, on a side facing the positioning device, a front surface that is a front limit of the radiation therapy apparatus toward the positioning device, and that in the first operating mode, the radiation head is behind the front surface viewed from the positioning device, and
    wherein the extension mechanism is configured such that, in a second operating mode of the radiation therapy apparatus, the radiation head, viewed from the positioning device, is movable to be in front of the front surface that in the first operating state is the front limit.

2. The radiation therapy apparatus as claimed in claim 1, wherein the gantry has, on a side facing away from the positioning device, a back surface that, in the first operating mode, is a rear limit of the gantry, and
    wherein the extension mechanism is configured, such that in a third operating mode of the radiation therapy apparatus, the radiation head is movable, using the extension mechanism, to be behind the back surface viewed from the positioning device.

3. The radiation therapy apparatus as claimed in claim 2, wherein the gantry is tiltable about a horizontal axis.

4. The radiation therapy apparatus as claimed in claim 2, wherein the central aperture of the gantry has a longitudinal axis, and
    wherein the extension mechanism enables a translatory movement of the radiation head along a direction having a component along the longitudinal axis.

5. The radiation therapy apparatus as claimed in claim 2, wherein the extension mechanism is extendable out along an isocentric circular segment.

6. The radiation therapy apparatus as claimed in claim 1, wherein the gantry is tiltable about a horizontal axis.

7. The radiation therapy apparatus as claimed in claim 6, wherein the central aperture of the gantry has a longitudinal axis, and
wherein the extension mechanism enables a translatory movement of the radiation head along a direction having a component along the longitudinal axis.

8. The radiation therapy apparatus as claimed in claim 1, wherein the central aperture of the gantry has a longitudinal axis, and
wherein the extension mechanism enables a translatory movement of the radiation head along a direction having a component along the longitudinal axis.

9. The radiation therapy apparatus as claimed in claim 8, wherein the extension mechanism is configured such that, in addition to the translatory movement, a tilting movement of the radiation head that tilts the radiation head relative to the extension mechanism is executable.

10. The radiation therapy apparatus as claimed in claim 8, wherein the extension mechanism provides only a translatory movement of the radiation head in the direction of the longitudinal axis.

11. The radiation therapy apparatus as claimed in claim 10, wherein the extension mechanism is configured such that, in addition to the translatory movement, another movement of the radiation head is executable, the other movement having a component in a direction perpendicular to the translatory movement.

12. The radiation therapy apparatus as claimed in claim 10, wherein the extension mechanism is configured such that, in addition to the translatory movement, a tilting movement of the radiation head that tilts the radiation head relative to the extension mechanism is executable.

13. The radiation therapy apparatus as claimed in claim 10, wherein the extension mechanism is extendable out along an isocentric circular segment.

14. The radiation therapy apparatus as claimed in claim 8, wherein the extension mechanism is configured such that, in addition to the translatory movement, another movement of the radiation head is executable, the other movement having a component in a direction perpendicular to the translatory movement.

15. The radiation therapy apparatus as claimed in claim 14, wherein the extension mechanism is configured such that, in addition to the translatory movement, a tilting movement of the radiation head that tilts the radiation head relative to the extension mechanism is executable.

16. The radiation therapy apparatus as claimed in claim 14, wherein the extension mechanism is configured such that the radiation head is alignable to an isocentric emission of a beam of the therapeutic radiation.

17. The radiation therapy apparatus as claimed in claim 6, wherein the extension mechanism is extendable out along an isocentric circular segment.

18. The radiation therapy apparatus as claimed in claim 8, wherein the extension mechanism is configured such that the radiation head is alignable to an isocentric emission of a beam of the therapeutic radiation.

19. The radiation therapy apparatus as claimed in claim 1, wherein the extension mechanism is extendable out along an isocentric circular segment.

20. The radiation therapy apparatus as claimed in claim 1, wherein the extension mechanism is configured such that the radiation head is alignable to an isocentric emission of a beam of the therapeutic radiation.

* * * * *